(12) United States Patent
Puno

(10) Patent No.: US 8,313,514 B2
(45) Date of Patent: Nov. 20, 2012

(54) DEVICE FOR INTERCONNECTION OF COMPONENTS IN A SPINAL IMPLANT ASSEMBLY

(75) Inventor: Rolando M. Puno, Prospect, KY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1666 days.

(21) Appl. No.: 11/434,447

(22) Filed: May 15, 2006

(65) Prior Publication Data

US 2007/0276367 A1 Nov. 29, 2007

(51) Int. Cl.
*A61B 17/70* (2006.01)

(52) U.S. Cl. ........................................ 606/250

(58) Field of Classification Search .................. 606/246, 606/250–253, 260, 264, 270, 272, 276–279, 606/300; 411/95, 97; 403/9, 49
See application file for complete search history.

(56) References Cited

U.S. PATENT DOCUMENTS

| | | | |
|---|---|---|---|
| 5,624,442 | A | 4/1997 | Mellinger et al. |
| 5,709,685 | A | 1/1998 | Dombrowski et al. |
| 6,171,311 | B1 | 1/2001 | Richelsoph |
| 6,238,396 | B1 | 5/2001 | Lombardo |
| 2002/0111625 | A1 | 8/2002 | Richelsoph et al. |
| 2003/0114853 | A1 | 6/2003 | Burgess et al. |
| 2004/0049188 | A1 | 3/2004 | Slivka et al. |
| 2005/0090821 | A1 | 4/2005 | Berrevoets et al. |
| 2005/0192569 | A1 | 9/2005 | Nichols et al. |
| 2005/0228377 | A1 | 10/2005 | Chao et al. |
| 2007/0043365 | A1 | 2/2007 | Ritland |
| 2007/0225712 | A1 | 9/2007 | Altarac et al. |

*Primary Examiner* — Alvin Stewart
*Assistant Examiner* — David Comstock

(57) ABSTRACT

A spinal fixation system including an interconnection device is provided. The interconnection device comprises a connector element including a passage structured to receive a component of the spinal fixation system therein. The passage is at least partially bound by a first wall portion and a second wall portion, wherein the first wall portion is movable between a first position to receive the component and a second position to restrain the component in the passage. The device further includes a retainer element which holds the first wall portion in the second position in order to lock the component in the passage.

31 Claims, 4 Drawing Sheets

DEVICE FOR INTERCONNECTION OF COMPONENTS IN A SPINAL IMPLANT ASSEMBLY

FIELD OF THE INVENTION

The present invention relates generally to the field of orthopedic devices, and more particularly, but not exclusively, relates to a device for the interconnection of components in a spinal implant assembly.

BACKGROUND

The present invention relates to a prosthetic device and a manner of using the same, and more particularly, but not exclusively, relates to the interconnection of components to assemble an orthopedic construct for treatment of a spinal deformity.

The use of prosthetic implants to address orthopedic injuries and ailments has become commonplace. In this arena, it is often desired to decrease the invasiveness of the procedures, improve implant integrity, and provide more positive patient outcomes. Some of these implants depend on interconnection between various system components. Unfortunately, current interconnection devices can be limiting in certain applications.

Thus, there remains a need for an improved device for the interconnection of components in a spinal implant assembly. The present invention satisfies this need and provides other benefits and advantages in a novel and unobvious manner.

SUMMARY

The present invention relates generally to the field of orthopedic devices, and more particularly relates to a device for the interconnection of components in a spinal implant assembly. While the actual nature of the invention covered herein can only be determined with reference to the claims appended hereto, certain forms of the invention that are characteristic of the preferred embodiments disclosed herein are described briefly as follows.

In one form of the present invention, a device is provided that interconnects components of a spinal implant system. The device contains a connector element with a passage structured to receive a portion of the component of the spinal implant system. A first wall portion and a second wall portion partially surround the passage with the first wall portion being capable of transitioning between a first configuration to receive the portion of the component and a second configuration to secure the portion of the component in the passage. The device further includes a retainer element which cooperates with the connector element to maintain the first wall portion in a particular configuration. In one embodiment of the present application the first wall is maintained in the second configuration to secure the portion of the component in the passage.

In a further form of the present invention, a device is provided for interconnecting components of a spinal implant system. The device includes an elongated body comprising a first end which defines a first connector and a second end which defines a second connector. Each of the first connector and the second connector are integrally formed with the elongated body and each includes a passage therethrough. Each passage is integrally formed from a respective connector and is further defined as being sized to receive a portion of a component of the spinal implant system. A flexibly deformable wall encloses the passage but for one section including an opening. The wall is capable of transitioning from a first configuration arranged to transversely receive the portion of the component and a second configuration arranged to lock the portion of the component in the passage. A pair of retainer elements is further provided to cooperate with the connector elements to influence and retain the wall in the second configuration. When the wall is retained in the second configuration the portion of the component in the passage is secured therein.

In another form of the present invention, a device for interconnecting various components of a spinal implant system is provided. The device includes a connector element including a component seating portion formed by at least a first and second wall. The component seating portion is in communication with an opening between the first and second walls and is structured to receive a portion of the component therein. The first wall is further capable of movement in a first direction to a first position which expands the component seating portion at the opening to receive the portion of the component. A second direction of movement of the first wall is further provided to contract the component seating portion to a second position in order to capture the portion of the component therein. The device also includes a retainer element for selectively maintaining the first wall in the second position to secure the portion of the component in the component seating portion.

In yet a further form of the present invention, a device is provided for interconnecting components of a spinal fixation system. This device includes an elongated body wherein one or more of its ends define a connector element including a passage. The passage is defined by a first wall, a second wall, and a closed end which is formed by part of the connector element. Opposite the closed end is an open end situated between the first and second walls. The first wall is capable of moving in a direction which expands the opening to a first configuration to receive a portion of the component. Another direction of movement is provided for the first wall such that it moves to contract the passage and opening at a second configuration to capture the portion of the component in the passage. A retainer element which cooperates with the connector element selectively maintains the first wall in the second configuration to secure the portion of the component in the passage.

It is one object of the present invention to provide an improved device for the interconnection of components in a spinal implant assembly. Further objects, features, advantages, benefits, and aspects of the present invention will become apparent from the drawings and description contained herein.

DESCRIPTION OF THE PREFERRED EMBODIMENTS

Figure 1:
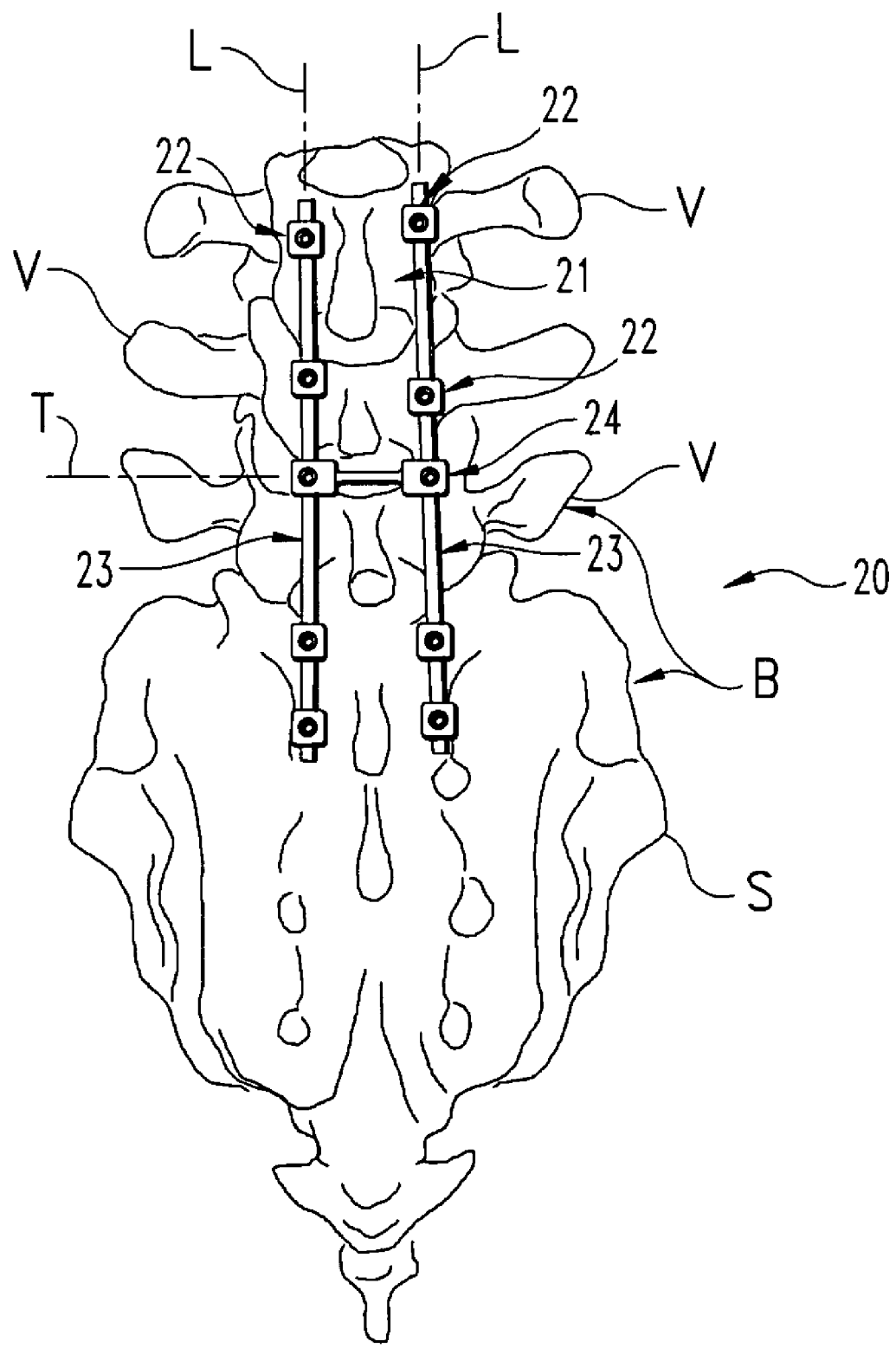
FIG. 1 is a posterior view of the spinal column illustrating a spinal fixation system.

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Referring to FIG. 1, there is shown therein posterior spinal fixation system 20 of one embodiment of the application located at a desired skeletal location of a patient. More specifically, as depicted in FIG. 1, system 20 is affixed to bones B of the spinal column 21 from a posterior approach. Bones B include the sacrum S and several vertebrae V. System 20 generally includes several bone attachment devices 22 and rods 23 structured to selectively interconnect with bone attachment devices 22. In system 20, bone attachment devices 22 are affixed to various locations of the spinal column 21 and interconnected with rods 23. Various components of system 20, including rods 23 and bone attachment devices 22, may be interconnected by an interconnection device 24 to provide a stable construct for treating spinal disorders. Posterior fixation system 20 may be used for, but is not limited to, treatment of degenerative spondylolisthesis, fracture, dislocation, scoliosis, kyphosis, spinal tumor, and/or a failed previous fusion.

Bone attachment devices 22 may be, but are not limited to, multi-axial, poly-axial, uni-axial, or uni-planar bone screws having a threaded stem portion opposite a head portion including a rod receiving portion, where the threaded stem and the head portion are movable relative to one another. The threaded stem of these bone screws is structured to threadingly engage a passageway prepared in one or more bones or bony structures in a standard manner, and can be provided with cutting flutes or other structure for self-tapping and/or self-drilling capabilities. The threaded stem can also be cannulated to receive a guidewire to facilitate placement and may further include fenestrations or other openings for placement of bone growth material. In one movable form, the threaded stem and the head portion are engaged together with a "ball and joint" or swivel type of coupling that permits relative movement therebetween during at least some stages of assembly. In yet another form, bone attachment devices 22 may include one or more hooks to engage an adjacent bony structure such as a pedicle, lamina, spinous process, transverse process, or other bony structure suitably engaged with a spinal hook. For instance, a multi-axial laminar hook form of device 22 can be used in place of a bone screw. In still other embodiments, device 22 can include a bone attachment structure in the form of a staple, bone plate, interbody fusion device, interbody spacer, spinal anchor, intravertebral fusion device, bone clamp, or other anchor. In one form bone attachment devices 22 are made of medical grade stainless steel but other embodiments may be composed of, but are not limited to, titanium, a titanium alloy or other metallic alloy, and/or a nonmetallic composition In addition, rod 23 may be solid or hollow along some or all of its length and/or may be of homogenous or heterogeneous composition. Rod 23 can be rigid, or be flexible or include one or more flexible portions to permit at least limited spinal motion. Rod 23 may be substituted with any suitable spinal stabilization element positionable along the spinal column, including plates, tethers, wires, cables, cords, inflatable devices, expandable devices, and formed in place devices, for example.

Figure 2:
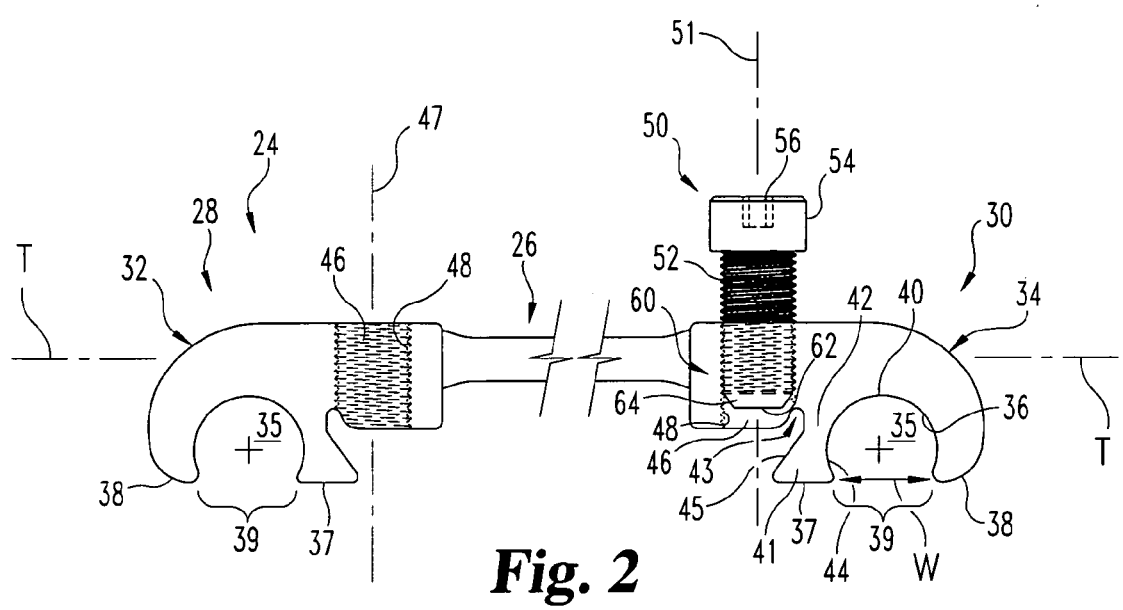
FIG. 2 is a side elevational view of an interconnection device according to one form of the present invention.

FIG. 2 is a side elevational view of interconnection device 24 according to one form of the present application, wherein like numerals refer to like features previously described. Interconnection device 24 includes an elongated body 26 extending along longitudinal axis L. Elongated body 26 includes a first end 28 opposite a second end 30 with each further defining a first connector 32 and a second connector 34, respectively. In alternative embodiments not shown, first end 28 or second end 30 include either first connector 32 or second connector 34 as illustrated in FIG. 2, while the opposing end includes an alternatively structured connector not shown. Each of first connector 32 and second connector 34 includes an engagement portion 36 structured to receive a component of system 20, wherein each engagement portion 36 is disposed on the same side of connectors 32, 34. Engagement portion 36 is generally formed by a first wall 37 and a second wall 40, wherein each of first wall 37 and second wall 40 individually extend from first connector 32 and second connector 34. In the embodiment illustrated, each of first wall 37 and second wall 40 is integrally formed from first connector 32 and second connector 34. However, in alternative embodiments not shown, it is contemplated that all or part of first wall 37 and second wall 40 may be formed from a material different than that of first connector 32 and second connector 34.

Further defining engagement portion 36 is a closed end 42. While closed end 42 is illustrated as being formed by a section of connectors 32 and 34, it should be understood that closed end 42 may be formed as a continuation of first wall 37 and second wall 40, such that closed end 42 is not in direct contact with connectors 32 and 34. In deed, in one form closed end 42 may be in the form of a third wall which extends between first wall 37 and second wall 40. In any of these forms, closed end 42 may be in direct contact with connector 32 or 34, or spaced apart therefrom in order to achieve a desirable height of interconnection device 24 relative to components of system 20. As shown, engagement portion 36 is substantially circular in sectional profile, structured to receive for example, rod 23 of system 20 when rod 23 has a circular sectional profile. It should be understood however that the section profile of rod 23 may change, and as the sectional profile of rod 23 changes, the shape and structure of engagement portion 36 also changes. In deed, in alternative embodiments not shown, engagement portion 36 may even be structured to receive alternative components of system 20 not shown.

As illustrated, first wall 37 includes an enlarged end portion 37a opposite a smaller section 38 which is located near a relief section 44 including surfaces 44a and 44b. Relief section 44 is provided so that first wall 37 is moveable in two directions, as indicated by directional arrows A and B. It should be understood that each of directional arrows A and B do not correspond to directions generally. Arrow A corresponds to a direction of movement of first wall 37 toward second wall 40 while arrow B corresponds to a direction of movement of first wall 37 away from second wall 40. As force is applied from one direction first wall 37 moves toward second wall 40 in the direction of arrow A, closing opening 43 and contracting engagement portion 36. As movement occurs in direction A, surface 44a moves away from surface 44b in relief section 44. Additionally, as force is applied from an alternative direction first wall 37 moves away from second wall 40 in the direction of arrow B, stretching opening 43 and expanding engagement portion 36. As movement occurs in direction B, surface 44a moves toward surface 44b in relief section 44. Relief section 44 may be larger or smaller than as depicted and it should be appreciated that its size will alter in relation to the amount of movement desired in either direction A or B. For example, if a greater range of motion is desired in direction B, the distance between surfaces 44a and 44b of relief section 44 will be greater.

In addition to relief section 44, all or part of first wall 37 may be formed of a flexible material to aid in the movement of first wall 37 for expanding and contracting engagement portion 36. For example, the material comprising section 38 may be flexible while the material comprising end portion 37a remains rigid and inflexible. In alternative embodiments not shown, one or both of first connector 32 and second connector 34 may not include relief section 44. In these embodiments, first wall 37 is flexibly deformable to allow for expansion and contraction of engagement portion 36. In these alternative embodiments, only a section of first wall 37 may be flexible or the entire portion of first wall 37 may be flexible. In some embodiments, first wall 37 may be made flexible upon some or all of its length by adding relief notches or holes thereto. Other manners known to those skilled in the art for providing flexibility to first wall 37 are further included in this application.

Interconnection device 24 further includes an aperture 46 extending transversely through each of first connector 32 and second connector 34. Aperture 46 further includes internal threading 48 as most clearly seen in first connector 32 in FIG. 2. Further included in interconnection device 24 is a retainer element 50 shown in the form of threaded fastener 51. Threaded fastener 51 includes an elongated threaded stem 52 opposite an enlarged head portion 54, wherein head portion 54 includes a tool engagement portion 56. Threaded stem 52 is structured to threadingly engage internal threading 48 such that as threaded fastener 51 is rotated, it moves transversely to second connector 34. While threaded fastener 51 is only shown in second connector 34, it should be understood that it is structured to engage aperture 46 of first connector 32 as well, and has only been omitted therefrom to enhance clarity of certain structural features. As illustrated, aperture 46 is adjacent relief section 44, but will vary in alternative embodiments. In one form aperture 46 can be placed at any position which will facilitate extension of threaded fastener 51 through aperture 46 to contact first wall 37. For example, as shown aperture 46 is arranged substantially perpendicular to longitudinal axis L, but in alternative embodiments may intersect longitudinal axis L at a number of angular variations. In one of these embodiments aperture 46 extends from where elongated body 26 joins connectors 32 and 34 to a position near first wall 37, so long as threaded fastener 51 is capable of extending through aperture 46 and contacting first wall 37.

Figure 3:
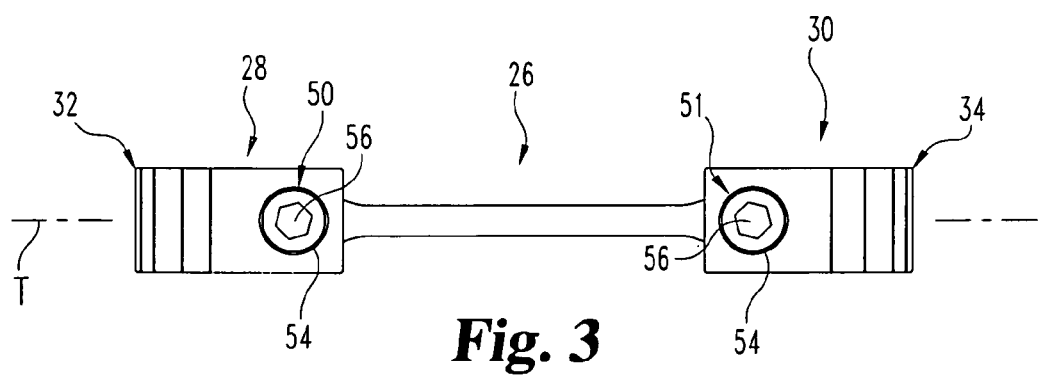
FIG. 3 is a top plan view of the interconnection device shown in FIG. 2.

Referring to FIG. 3, wherein like numerals refer to like features previously described, interconnection device 24 is shown in top plan view. As shown, each of threaded fasteners 51 is engaged with apertures 46 and includes tool engagement portion 56 in a hex or allen shape. In alternative embodiments tool engagement portion 56 may be square, phillips, slotted, or of any other form known to those skilled in the art. It should be further understood that as illustrated in both FIGS. 2 and 3, first connector 32 and second connector 34 are formed integral with elongated body 26. In these embodiments, each of elongated body 26, first connector 32, second connector 34, and engagement portion 36 are integrally formed. In alternative embodiments one or both of connectors 32, 34 may be connected to elongate body 26 in a different manner, including but not limited to threading, pinning, compression, welding, and/or adhesion.

Additionally, the length of interconnection device 24, as indicated by reference arrow C, is generally sized to span a distance between two components of system 20. In one embodiment the length of interconnection device 24 is sized to span and connect rods 23. In alternative embodiments not shown, interconnection device 24 may be formed of two members and include a linking/interconnection device that allows alteration of length as indicated by arrow C to appropriately span a desired distance between components. In still another alternative embodiment, the interconnection device provides for alterations of the angular orientation between the two members to provide adjustability in the positioning of interconnection device 24 between two components. It should be further understood that either first connector 32 or second connector 34 may be rotated relative to the other about longitudinal axis L. For example, while one connector is engaging a spinal rod extending longitudinal to spinal column 21 the other connector may be engaging a component extending transversely from spinal column 21, for instance, a bone screw having a stem or stud extending therefrom.

Figure 4:
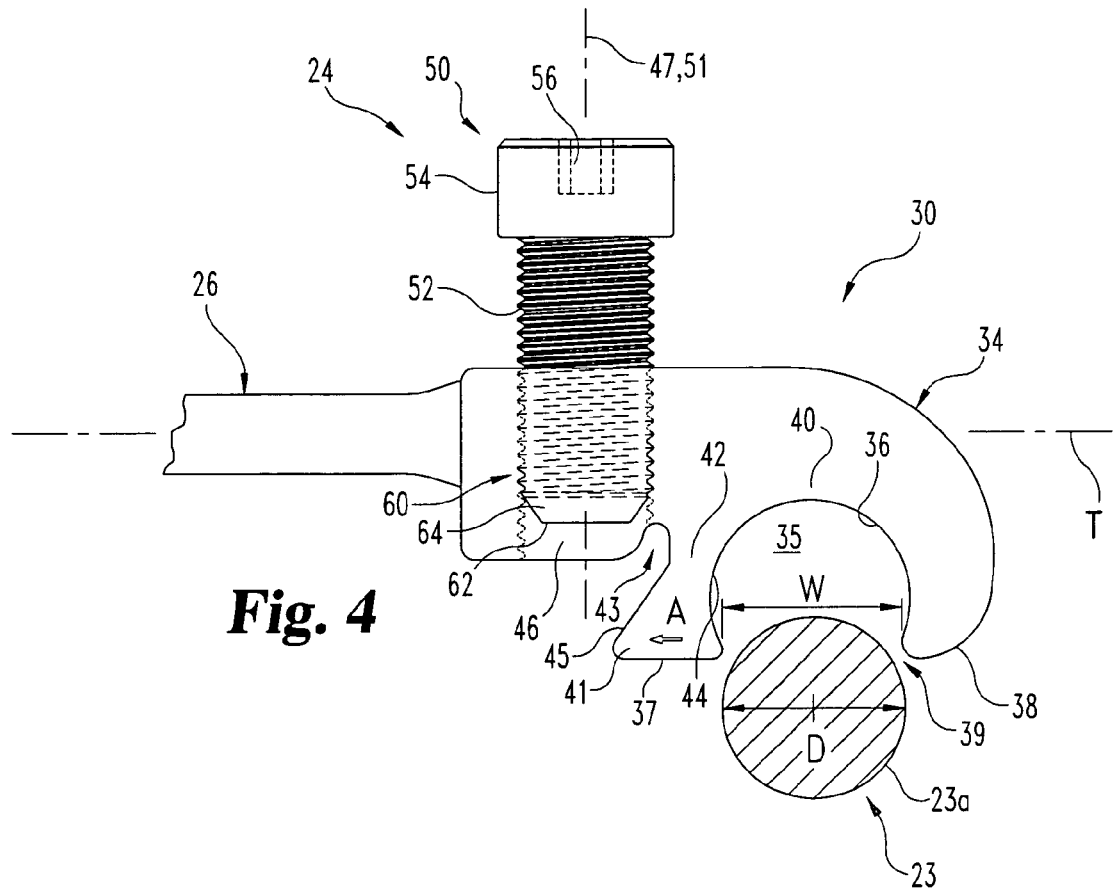
FIG. 4 is a side elevational view of an end portion of the interconnection device shown in FIG. 2, as positioned for engagement with a spinal rod.
Figure 5:
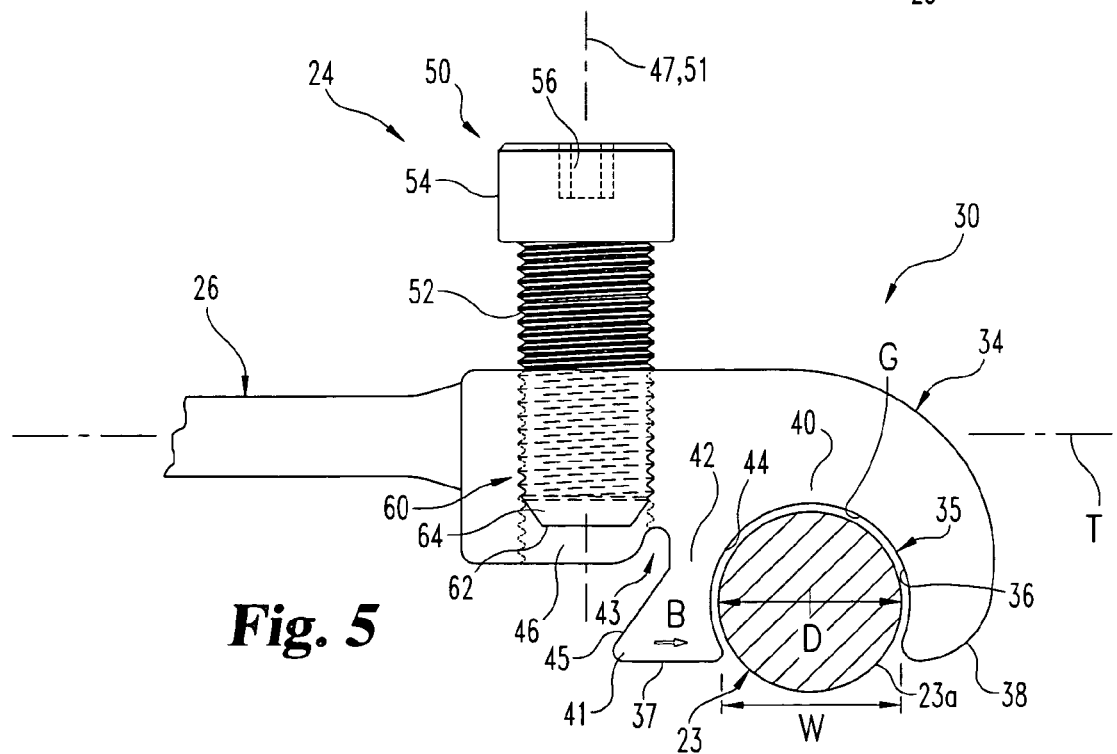
FIG. 5 is a side elevational view of the end portion of the interconnection device shown in FIG. 4, as provisionally engaged to the spinal rod.
Figure 6:
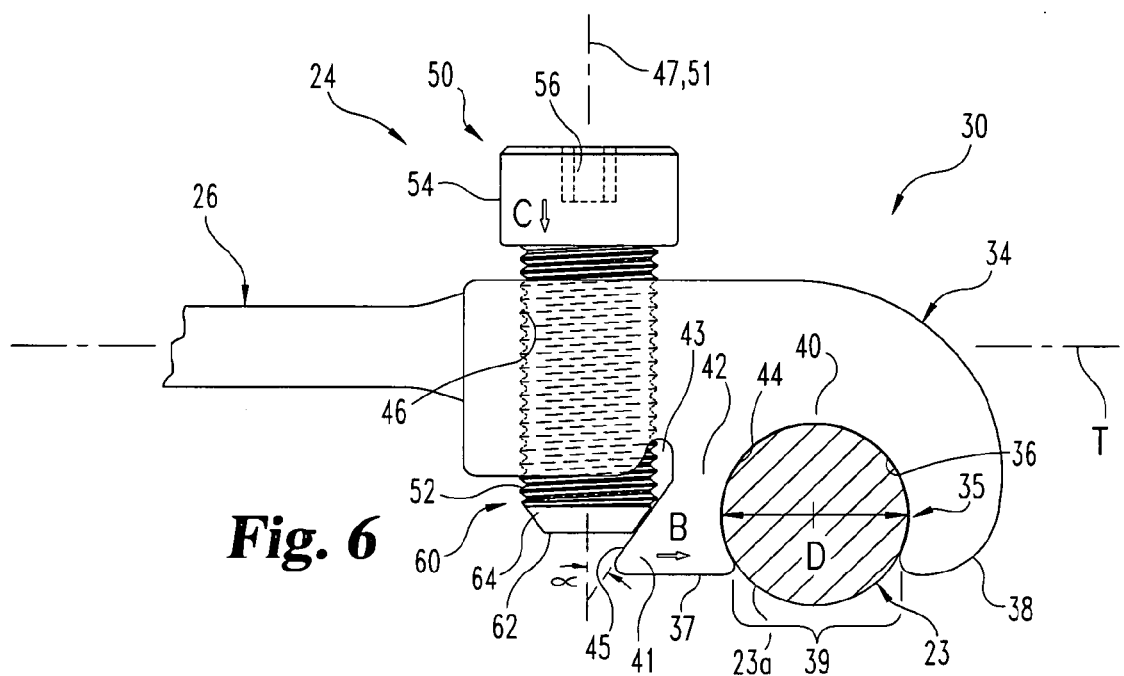
FIG. 6 is a side elevational view of the end portion of the interconnection device shown in FIG. 4, as securely engaged to the spinal rod.

Referring now to FIGS. 4, 5, and 6, where like numerals refer to like features previously described, there is illustrated the manner in which interconnection device 24 engages with a component of spinal system 20, wherein the component is in the form of spinal rod 23. It should be understood that in each of FIGS. 4, 5, and 6 second connector 34 is illustrated, but that the description directed to second connector 34 is similarly applicable to first connector 32. In specific regard to FIG. 4, there is shown a side elevational view of second connector 34 as positioned for engagement with spinal rod 23. As illustrated, rod 23 has a circular sectional profile including a diameter indicated by reference arrow D. Diameter D of rod 23 is larger than opening 43 between first wall 37 and second wall 40 in FIG. 4. As connector 34 is engaged with rod 23, the outer surface 23a of rod 23 contacts point 39 of first wall 37 and point 40a of second wall 40. As further pressure is applied, outer surface 23a begins to move first wall 37 away from second wall 40 at opening 43 in direction B. While first wall 37 moves in direction B surface 44a of relief section 44 simultaneously moves toward surface 44b. As this happens, opening 43 becomes larger such that engagement portion 36 may receive rod 23 therein. In this embodiment relief section 44 provides the flexibility necessary in order for first wall 37 to move enough to allow rod 23 to pass entirely through opening 43 and into engagement portion 36 as is illustrated in FIG. 5. However, if increased flexibility of first wall 37 is desired then relief section 44 may be altered or part of first wall 37 may be flexible, as herein already described. Once rod 23 has sufficiently passed point 39 and point 40, first wall 37 correspondingly moves in direction A until rod 23 is entirely seated in engagement portion 36 and opening 43 is back to its original position, as also shown in FIG. 5. As first wall 37 moves back to its original position, surface 44a moves away from surface 44b in relief section 44.

Once rod 23 is completely received in engagement portion 36 a space remains between outer surface 23a of rod 23 and first wall 37 and second wall 40, as indicated by reference numerals 41 and 41a respectively, as shown in FIG. 5. In this form interconnection device 24 may be freely moved along rod 23 to a desired location without removing second connector 34 from rod 23. In order to eliminate spaces 41 and 41a and to restrict movement of interconnection device 24 along rod 23, threaded fastener 51 may be engaged with aperture 46 and extended therethrough to influence first wall 37 toward second wall 40 at opening 43. As illustrated in FIG. 6 threaded fastener 51 is further defined at its tip 60 by a flat section 62 and a tapered section 64. First wall 37 includes a tapered retainer contact area 58 which corresponds to tapered section 64. As threaded fastener 51 is rotated in aperture 46 it moves toward contact area 58 such that tapered section 64 communicates with contact area 58. Further engagement of threaded fastener 51 moves tapered section 64 further down contact area 58 bearing against first wall 37 and forcing it toward second wall 40 in direction A while surface 44a moves further away from surface 44b in relief section 44. As this occurs, point 39 influences rod 23 toward point 40a until rod 23 is securely retained in engagement portion 36 and spaces 41 and 41a are eliminated. When fully engaged, head 54 of threaded fastener 51 is in contact with connector 34 and connector 34 and rod 23 are secured in a rigid construct.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A device for interconnection of components in a spinal implant assembly, comprising:
    a connector element including a passage sized to receive a portion of the component therein, said passage at least partially bound by a connector wall extending along an axis, a movable first wall portion and a stationary second wall portion each extending transversely from said connector wall, said connector wall including an upper end surface, an opposite lower end surface and an aperture extending transversely and entirely through said connector wall from said upper end surface to said lower end surface, wherein said first wall portion is integrally and unitarily formed with said connector element and is transitionable between a first configuration adapted to receive said portion of the component within said passage and a second configuration adapted to capture said portion of the component within said passage; and
    a retainer element positioned within and movable through said aperture and including a distal tip portion that extends out of said aperture beyond said lower end surface of said connector wall and into contact with an exterior outer surface of said first wall portion of said connector element to thereby displace said first wall portion toward said second wall portion while maintaining said second wall portion in a stationary position relative to said first wall portion and to selectively maintain said first wall portion in said second configuration to capture said portion of the component within said passage.

2. The device of claim 1, wherein said passage is integrally formed with said connector element.

3. The device of claim 1, wherein said component is a longitudinal member.

4. The device of claim 1, wherein said aperture comprises a threaded aperture located adjacent said first wall portion.

5. The device of claim 4, wherein said first wall portion includes a terminal end and an inner surface and said exterior outer surface, said inner surface facing said passage and being structured to engage with said portion of the component, and said exterior outer surface including a retainer contact area engaged with said distal tip portion of said retainer element.

6. The device of claim 5, wherein said retainer element is a threaded fastener including a head opposite a threaded stem, said threaded stem being structured to engage said threaded aperture and to extend through said connector element with said distal tip portion positioned to bear against said retainer contact area of said first wall portion to force said inner surface of said first wall portion toward said portion of the component to retain said portion of the component in said passage.

7. The device of claim 5, wherein said retainer contact area tapers relative to said axis from said terminal end toward said connector element.

8. The device of claim 7, wherein said retainer element is a threaded fastener including a head opposite a threaded stem, said threaded stem being structured to engage said threaded aperture and to extend through said connector element with said distal tip portion positioned to bear against said retainer contact area of said first wall portion to force said inner surface of said first wall portion toward said portion of the component to retain said portion of the component in said passage.

9. A device for interconnection of components in a spinal implant assembly, comprising:
    an elongate body extending along a longitudinal axis and including a first end and a second end wherein said first end defines a first connector element integrally formed with said elongate body and said second end defines a second connector element integrally formed with said elongate body, said first connector element and said second connector element each including a passage sized to receive a portion of the component therein, each said passage bound by a connector wall extending along said longitudinal axis, a flexibly deformable first wall portion and a second wall portion each extending transversely from said connector wall, said connector wall including an upper end surface, an opposite lower end surface and an aperture extending transversely and entirely through said connector wall from said upper end surface to said lower end surface, and wherein said passage includes an open end and is said flexibly deformable first wall portion is transitionable between a first configuration which allows said portion of the component to be received transversely through said open end and into said passage and a second configuration adapted to capture said portion of the component within said passage; and
    a retainer element positioned within said aperture in each of said first connector element and said second connector element, said retainer element movable through said aperture and including a distal tip portion that extends out of said aperture beyond said lower end surface of said connector wall and into contact with an exterior outer bearing surface of said first wall portion to thereby displace said first wall portion toward said second wall portion while maintaining said second wall portion in a stationary position relative to said first wall portion and to selectively maintain said first wall portion in said second configuration to capture said portion of the component within said passage.

10. The device of claim 9, wherein said elongate body is structured to span a distance between said components of said spinal implant assembly.

11. The device of claim 9, wherein said retainer elements are threaded fasteners.

12. The device of claim 9, wherein said components are longitudinal extending members.

13. The device of claim 9, wherein said components are spinal rods.

14. The device of claim 9, wherein said aperture in each of said first and second connector elements comprises a threaded aperture.

15. The device of claim 14, wherein said retainer elements are threaded fasteners, said threaded fasteners being structured to be threadingly advanced through respective ones of said threaded aperture in said first and second connector elements.

16. The device of claim 15, wherein said threaded aperture is positioned adjacent to said flexibly deformable first wall portion.

17. A device for interconnection of components in a spinal implant assembly comprising:
   a connector element including a component seating portion formed by a connector wall extending along an axis, a first wall and a second wall each extending transversely from said connector wall and axially spaced apart to define an opening therebetween, said connector wall including an upper end surface, an opposite lower end surface and an aperture extending transversely and entirely through said connector wall from said upper end surface to said lower end surface, said component seating portion being structured to receive a portion of the component within said opening between said first wall and said second wall and wherein said first wall moves to a first position to receive said portion of the component in said opening and further moves to a second position to capture said portion of the component in said opening of said component seating portion; and
   a retainer element positioned within and movable through said aperture in said connector wall and including a distal tip portion that extends out of said aperture beyond said lower end surface and into contact with an exterior outer surface of said first wall to thereby displace said first wall toward said second wall while maintaining said second wall in a stationary position relative to said first wall and to selectively maintain said first wall in said second position to secure said portion of the component in said opening of said component seating portion.

18. The device of claim 17, wherein said first wall extends from said lower end surface of said connector wall.

19. The device of claim 17, wherein said connector element further includes a retainer cooperation section and a deflection area.

20. The device of claim 19 wherein said deflection area is proximal to said first wall and is structured to permit movement of said first wall at said opening.

21. The device of claim 20 wherein said retainer cooperation area is proximal to said deflection area.

22. The device of claim 21 wherein said retainer cooperation area includes said retainer element and said retainer element communicates with said first wall to move said first wall toward said second wall to secure said portion of the component in said opening of said component seating portion.

23. The device of claim 17 wherein said connector element further includes a retainer cooperation area, said retainer cooperation area being proximal to said first wall.

24. The device of claim 23 wherein said retainer cooperation area includes said retainer element and said retainer element communicates with said first wall to move said first wall toward said second wall to secure said portion of the component in said opening of said component seating portion.

25. The device of claim 17 wherein said components are longitudinal members in the form of spinal rods, said longitudinal members each extending along a longitudinal axis arranged substantially perpendicular to said axis of said connector wall.

26. A device for interconnection of components in a spinal implant assembly comprising:
   an elongate body extending along a longitudinal axis and including a first end and second end and wherein one or more of said first end and said second end defines a connector element, said connector element including a passage defined by a connector wall extending along said longitudinal axis and defining a closed end of said connector element, a first wall and a second wall each extending transversely from said connector wall, said connector wall including an upper end surface, an opposite lower end surface and an aperture extending transversely and entirely through said connector wall from said upper end surface to said lower end surface, said passage being in communication with an opening between said first wall and said second wall at an open end of said connector element opposite said closed end, and wherein said first wall includes an exterior bearing surface positioned opposite an interior arcuate surface and translates to expand said opening to a first configuration to receive a portion of said component at said opening and translates to contract said opening and said passage to a second configuration to capture said portion of said component in said passage, wherein in said second configuration said bearing surface extends obliquely to said longitudinal axis; and
   a retainer element that is positioned within and movable through said aperture and including a distal tip portion that extends out of said aperture beyond said lower end surface of said connector wall below said closed end and into contact with said bearing surface to thereby displace said first wall toward said second wall while maintaining said second wall in a stationary position relative to said first wall and to selectively maintain said first wall in said second configuration to secure said portion of the component in said passage.

27. The device of claim 26, wherein said elongate body, said connector element, and said passage are integrally formed.

28. The device of claim 26, wherein said first wall is flexibly deformable.

29. The device of claim 28, wherein said connector element further includes a deflection area adjacent said first wall, said deflection area permitting flexibly deformable latitudinal movement of said first wall at said opening.

30. The device of claim 29, wherein said second wall is inflexible.

31. The device of claim 26, wherein said retainer element adjustably extends through said connector element proximal to said first wall, said retainer element further influencing said first wall toward said second wall at said opening to maintain said passage in said second configuration.

* * * * *